United States Patent [19]

Long et al.

[11] Patent Number: 5,607,930
[45] Date of Patent: Mar. 4, 1997

[54] 1,4-DISUBSTITUTED PIPERAZINES USEFUL IN THE THERAPY OF THE ASTHMA AND OF THE INFLAMMATION OF THE RESPIRATORY TRACT

[75] Inventors: Giorgio Long; Silvano Spinelli; Antonella Rozzi; Simonetta D'Alo'; Licia Gallico, all of Milano, Italy

[73] Assignee: Boehringer Mannheim Italia, S.p.A., Italy

[21] Appl. No.: 406,900

[22] PCT Filed: Aug. 24, 1993

[86] PCT No.: PCT/EP93/02264

§ 371 Date: Mar. 28, 1995

§ 102(e) Date: Mar. 28, 1995

[87] PCT Pub. No.: WO94/07856

PCT Pub. Date: Apr. 14, 1994

[30] Foreign Application Priority Data

Sep. 30, 1992 [IT] Italy .................. MI92A2263

[51] Int. Cl.⁶ .................. A61K 31/495; A61K 31/40; C07D 403/00; C07D 403/02
[52] U.S. Cl. .................. 514/235.8; 514/242; 514/245; 514/252; 544/113; 544/121; 544/122; 544/212; 544/295; 544/364; 544/372

[58] Field of Search .................. 544/113, 121, 544/122, 212, 295, 364, 372; 514/235.8, 242, 245, 252

[56] References Cited

U.S. PATENT DOCUMENTS 5,453,423   9/1995   Long et al. .................. 514/211

FOREIGN PATENT DOCUMENTS

92/18478   10/1992   WIPO.

*Primary Examiner*—Matthew V. Grumbling
*Attorney, Agent, or Firm*—Nikaido, Marmelstein, Murray & Oram, LLP

[57] ABSTRACT

Compounds of formula (I):

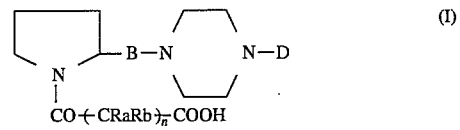

wherein Ra, Rb, B and D have the meanings reported in the disclosure, processes for making the same, and methods of using the same in the treatment of asthma and/or inflammation of the respiratory tract are disclosed.

12 Claims, No Drawings

1,4-DISUBSTITUTED PIPERAZINES USEFUL IN THE THERAPY OF THE ASTHMA AND OF THE INFLAMMATION OF THE RESPIRATORY TRACT

This is a national stage entry application of International PCT Application Serial PCT/EP93/02264, filed on Aug. 24, 1993 and published as WO94/07856 on Apr. 14, 1994.

The present invention relates to heterocyclic amines, a process for the preparation thereof and pharmaceutical compositions containing them.

More particularly, the invention relates to compounds of formula (I).

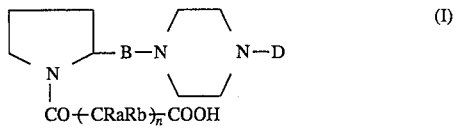

the single enantiomeric and diastereomeric forms thereof, the mixtures thereof and the salts thereof with pharmaceutically acceptable acids and bases, wherein:

B is a —CO—, —$CH_2OCO$—, —$CH_2OCS$—, —$CH_2NHCO$—, —$CH_2NHCS$— group;

D is a 5–6 membered heterocycle with 1–3 nitrogen atoms optionally substituted with 1 or 2 amino, mono-$C_1$–$C_6$-alkylamino, mono-$C_3$–$C_7$-alkenyl- or mono-$C_3$–$C_7$alkynylamino, di -$C_1$–$C_6$-alkylamino, ($C_1$–$C_6$)alkyl ($C_3C_7$)alkenylamino, piperidin-1-yl, morpholin-4-yl, pyrrolidin-1-yl groups;

Ra and Rb are hydrogen, $C_1$–$C_3$alkyl or, taken together with the carbon atom they are linked to, they form a $C_3$–$C_6$-cycloalkyl group;

n is an integer from 1 to 4.

Examples of $C_1$–$C_3$ or $C_1$–$C_6$-alkyl groups are methyl, ethyl, n-propyl, isopropyl, n-butyl, t-butyl, n-pentyl, n-hexyl.

Examples of 5- or 6-membered heterocyclic groups with 1–3 nitrogen atoms, optionally substituted with 1–2amino groups, are: [2,6-bis(diethylamino)-4-pyrimidinyl], [2,6-bis(allylamino)-4-pyrimidinyl], [2,6-bis(amino)-4-pyrimidinyl], [2,6-bis(pyrrolidin-1-yl)-4-pyrimidinyl], [4,6-bis(allylamino)-1,3,5-triazin-2-yl], [4,6-bis(diethylamino)-1,3,5-triazin-2-yl], [4,6-bis(pyrrolidin-1-yl)-1,3,5-triazin-2-yl], [3,6-bis(diethylamino)pyridin-2-yl], [3,6-bis(pyrrolidin-1-yl)pyridin-2-yl], [3,6-bis(allylamino)pyridin-2-yl], [3,6-bis(propargylamino)pyridin-2-yl], [3,6-bis(N-ethyl-N-allylamino)pyridin-2-yl], [3-ethylaminopyridin-2-yl].

Examples of mono-$C_1$–$C_6$-alkylamino groups are methylamino, ethylamino, propylamino, isopropylamino, n-butylamino, t-butylamino.

Examples of mono-$C_3$–$C_6$-alkenyl- or mono-alkynylamino groups are allylamino, propargylamino.

Examples of di -$C_1$–$C_6$-alkylamino groups are dimethylamino, diethylamino, methylethylamino, methylpropylamino, methylisopropylamino, diisopropylamino, methyl n-butylamino.

Examples of ($C_1$–$C_6$)alkyl-($C_3$–$C_7$)alkenylamino groups are methylallylamino, ethylallylamino, propylallylamino, isopropylallylamino.

Ra and Rb are preferably hydrogen, methyl, ethyl or, if taken together with the carbon atom they are linked to, are a cyclopropyl, cyclopentyl or cyclohexyl group.

Particularly preferred compounds (I) are those in which B is a —CO— or —$CH_2OCO$— group; D is an heterocycle selected from the group consisting of [2,6-bis(pyrrolidin-1-yl)-4-pyrimidinyl], [4,6-bis(pyrrolidin-1-yl)-1,3,5-triazin-2-yl], [3,6-bis(diethylamino)-pyridin-2-yl ]and [3-ethylaminopyridin-2-yl ]; Ra, which is the same as Rb, is hydrogen or methyl and n is 1.

The acid and basic groups can be salified respectively with pharmaceutically acceptable bases and acids. The non toxic salts thus obtained fall within the scope of the invention, as well as the single enantiomers, diastereomers, diastereomeric mixtures and racemates of the compounds of formula (I). Compounds (I) can be salified with both inorganic and organic acids which are pharmaceutically acceptable, such as hydrochloric, hydrobromic, hydroiodic, phosphoric, metaphosphoric, nitric or sulfuric, acetic, ossalic, tartaric, citric, benzoic, glycolic, gluconic, glucuronic, succinic, maleic, fumaric acids, etc. The carboxy group can be salified with bases of various nature, with the only proviso that the salts are pharmaceutically acceptable. Examples of said salts comprise those with: ammonium, sodium, potassium, calcium, magnesium, aluminium, iron, zinc, copper, or salts with pharmaceutically acceptable organic bases such as arginine, lysine, histidine, methylamine, ethylamine, dimethylamine, dibenzylamine, morpholine, phenylglycin and D-glucosamine.

Prolinamides with piperazinquinazoline are described to be ACE-inhibitors (Sankyo Co., JP 82 91,987; C.A., 97:198218w, 1982). N-Carbamoylprolinamides with N-methylpiperazine are known to be filaricidal (Indian J. Chem., Sect. B, 1987, 26B(8), 748–751).

The compounds of the invention showed useful pharmacological properties, particularly as far as the treatment of bronchial hyper-reactivity is concerned.

Bronchial hyper-reactivity is a clinical symptom of asthma and it is believed to be a direct consequence of an abnormal and latent contractility and sensitivity of the bronchial mucosa.

Bronchial hyper-reactivity can cause acute crisis of asthma after physical practice, and/or after exposure to external stimuli such as the inhalation of fog, pollutants, allergens and autacoids.

The bronchial hyper-reactivity conditions may be simulated by an experimental model consisting in the PAF infusion (600 μg/l) in male guinea-pigs weighing 400–450 g, kept under forced ventilation under urethane and pancuronium bromide anaesthesia.

PAF, which is one of the most important mediators involved in the inflammatory process of the airways, after infusion for 1 hour, causes an hyperreactivity reaction (bronchocostriction) to specific and different substances.

The activity of the compounds of the invention, in the considered pharmacological model, is shown by the prevention of the PAF-induced hyper-reactivity, measured as increase of the pulmonary insufflatory pressure (measured according to the modified procedure of Konzett and Rossler, Naun. Schmied. Arch. Exper. Pathol. Pharmacol. 191, 71, 1970).

The compounds of the invention, which are administered 10 minutes before the PAF administration in dosages which vary between 2 and 50 μg/kg, demonstrate a protective action which lasts at least 4–6 hours and results in a reduction of the PAF-induced hyperreactivity. Such pharmacological effects are dose related.

From what has been shown above it is clear that the compounds of the invention can be used in human therapy in the treatment of asthmatic and obstructive conditions of the respiratory tract, in the treatment of inflammatory phlogosis. For the intended therapeutic uses, the compounds of the invention will be administered in the form of pharmaceutical compositions which can be prepared with conventional excipients and techniques such as, for example, those described in Remington's Pharmaceutical Sciences Handbook, Mack Pub. Co., N.Y., USA, 17th ed., 1985 adapted for administration by intramuscular, intravenous, oral, aerosol and rectal routes.

The daily dose will depend on several factors such as the gravity of the pathology and the condition of the patient: it will normally consist of 1 to 50 mg of a compound of formula (I) for a patient weighing 70 one or more times a day.

The compounds of formula (I) are prepared by reacting a compound of formula (II)

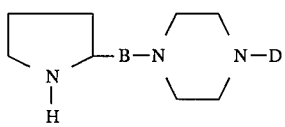
(II)

wherein B and D are as above defined, with a compound of formula (III)

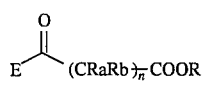
(III)

wherein Ra, Rb and n have the above described meanings; R is a $C_1-C_6$-alkyl, benzyl, allyl group or any other group which can easily be removed; E is halogen (chlorine, bromine), N-imidazolyl, OH, O-hydroxysuccinimidyl or, taken together with the carbonyl group, it forms a mixed anhydride with a carboxylic or sulfonic acid (for example, trifluoromethanesulfonic acid), to give compounds of formula (Ia)

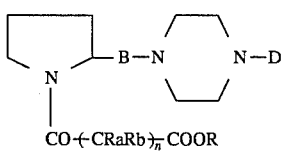
(Ia)

Compounds of formula (Ia) can be transformed into the compounds of formula (I) by means of conventional reactions such as:

a) when R is $C_1-C_6$-alkyl, hydrolysis with mineral bases such as sodium, potassium, lithium hydroxides at various concentrations and in various solvents (such as methanol, ethanol, dimethylformamide);

b) when R is allyl or benzyl, catalytic hydrogenation with various catalysts (such as palladium on charcoal in various concentrations, nikel-Raney, palladium tetrakis(triphenylphosphine), and the like) and in various solvents (such as methanol, ethanol, toluene, methylene chloride) or by means of hydrogen transfer procedures, such as those with ammonium formate, cyclohexene or sodium hypophosphite in the presence of palladium on charcoal in solvents such as water, lower alcohols or mixtures thereof.

The reaction of compound (II) with compound (III) is usually carried out in an inert solvent and in the presence of a suitable base. In case E—CO— is a carboxy group (E═OH), the reaction is carried out in an inert solvent and in the presence of condensing agents such as carbodiimides, isonitriles, and the like.

The preparation of the compounds of formula (II) is carried out starting from an acid of formula (IV)

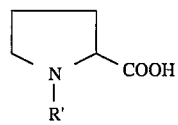
(IV)

wherein R' is a suitable protecting group which can be removed compatibly with the reactions described below and with the functional groups present in the molecule. Convenient protecting groups of formula R' can be: tert-butoxycarbonyl, methoxycarbonyl, 9-fluorenoxycarbonyl, 2,2,2-trichloroethoxycarbonyl, allyloxycarbonyl, benzyloxycarbonyl. Compounds of formula (IV) are commercially available or they can be prepared from proline by means of conventional and widely known reactions, which are reported in literature. If said compounds are not commercially available as the enantiomerically pure forms thereof, they can be resolved with conventional methods such as salification with optically active bases and separation of the diastereomeric salts.

The transformation of the products of formula (IV) in those of formula (V)

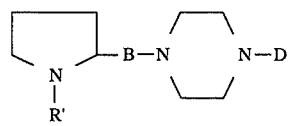
(V)

wherein R' has the above defined meanings, can be effected with conventional reactions.

Particularly:

a) the synthesis of compounds of formula (Va):

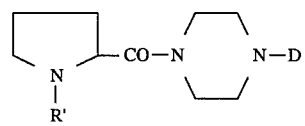
(Va)

starting from compounds of formula (IV), can be carried out by transformation of the carboxy group into a succinimido ester, acid chloride, mixed anhydride, imidazolide or other reactive derivatives of the carboxy group and condensation thereof with an amine of

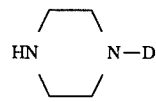
(VI)

b) the synthesis of compounds of formula (Vb):

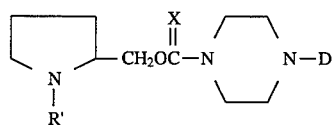
(Vb)

in which X═O or S, starting from compounds of formula (IV), can be performed by reduction of the carboxy group or of a corresponding mixed anhydride or a carboxy ester derivative thereof to primary alcohol ($CH_2OH$), which can be converted into a carbamate or thiocarbamate by reaction with carbonyldiimidazole or thiocarbonyldiimidazole and subsequently with an amine of formula (VI). The reduction of the carboxy group of proline or of a mixed anhydride thereof to alcohol can conveniently be carried out with reducing agents such as diborane or a borohydride of an alkali or alkaline-earth metal;

c) the synthesis of compounds of formula (Vc):

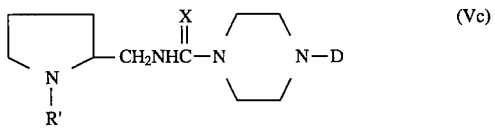

in which X=O or S, can be carried out by conversion of the alcohols, obtained as described in point b), into the corresponding amines according to the Mitsunobu's reaction using ditertbutylimino dicarboxylate as a nucleophilic agent and subsequent deprotection of the amino group with gas hydrochloric acid or with trifluoroacetic acid. The resulting amines can be converted into the corresponding ureas or thioureas by reaction with carbonyl- or thiocarbonyldiimidazole respectively and, subsequently, with an amine of formula (VI).

The transformation of compounds of formula (V) into compounds of formula (II) can be performed by conventional removing methods which are specific and selective for the used protecting group and particularly, in the case of BOC-derivatives, with trifluoroacetic acid or trimethylsilyl iodide.

Compounds of formula (III) are obtained according to conventional processes reported in literature.

The following examples and preparations further illustrate the invention. The concentrations are expressed as % in w/v. The described compounds should be considered as racemic mixtures, if not otherwise stated by means of the symbols (+) and (−). The malonic acid monoalkyl- or monobenzyl esters and the acyl chlorides thereof are known in literature or anyhow they can be prepared according to conventional methods which are widely reported in literature.

EXAMPLE 1

A solution containing 2.5 g of BOC-L-proline in anhydrous THF (10 ml) is added, at a temperature of 0° C., under inert gas atmosphere and with stirring, with 2.9 g of N-hydroxysuccinimide dissolved in 10 ml of THF. Said solution is added dropwise with a solution of 2.1 ml of morpholinoethylisonitrile in 5 ml of THF and stirring is continued at room temperature for 2 hours; the reaction mixture is acidified with 1N hydrochloric acid to acid pH (litmus paper) and is extracted with ethyl acetate (3×10 ml). The combined organic extracts are concentrated under vacuum to crystallize the BOC-L-proline succinimido ester, which is separated by filtration, to obtain 2.6 g, m.p. 128°–130° C. 1 g of the BOC-L-proline succinimido ester is dissolved in acetonitrile (7 ml), at room temperature and under inert gas atmosphere, then, under stirring, 0.97 g of N-[4,6-bis(pyrrolidin-1-yl)-1,3,5-triazin-2-yl]piperazine dissolved in acetonitrile (5 ml) are added. After 5 hours the reaction mixture is concentrated under vacuum to small volume, then it is added with a sodium bicarbonate saturated solution to slightly basic pH. The mixture is extracted with ethyl acetate (3×10 ml), then the combined extracts are concentrated to small volume under vacuum. By addition of ethyl ether, 1.5 g of (−)-N'-[(pyrrolidin-1-tertbutoxycarbonyl-2-yl)carbonyl]-N'-[4,6-bis(pyrrolidin-1-yl)-1,3,5-triazin-2-yl]piperazine precipitate, m.p. 148° C. after recrystallization from diisopropyl ether, $[\alpha]_D=-20.25°$ (c=2.01 in EtOH).

EXAMPLE 2

By reacting a solution of the BOC-proline N-hydroxysuccinimido ester in acetonitrile with a suitable N-substituted piperazine, according to the procedure described in example 1, the following N,N'-disubstituted piperazines are obtained:

N'-[(pyrrolidin-1-tertbutoxycarbonyl-2-yl)carbonyl]-N-[2,6-bis(diethylamino)pyrimidin-4-yl]piperazine, N'-[(pyrrolidin-1-tertbutoxycarbonyl-2-yl)carbonyl]-N-[2,6-bis(allylamino)pyrimidin-4-yl]piperazine, (−)-N'-[(pyrrolidin-1-tertbutoxycarbonyl-2-yl)carbonyl]-N-[2,6-bis(pyrrolidin-1-yl)pyrimidin-4-yl]piperazine, m.p. 168°–170° C., $[\alpha]_D=-20.7°$ (c=2 in EtOH), (+)-N'-[(pyrrolidin-1-tertbutoxycarbonyl-2-yl)carbonyl]-N-[2,6-bis(pyrrolidin-1-yl)pyrimidin-4-yl]piperazine, $[\alpha]_D=+20.2°$ (c=2.03 in EtOH), N'-[(pyrrolidin-1-tertbutoxycarbonyl-2-yl)carbonyl]-N-[2,6-bis(pyrrolidin-1-yl)pyrimidin-4-yl]piperazine, m.p. 125° C., N'-[(pyrrolidin-1-tertbutoxycarbonyl-2-yl)carbonyl]-N-[4,6-bis(allylamino)-1,3,5-triazin-2-yl]piperazine, N'-[(pyrrolidin-1-tertbutoxycarbonyl-2 -yl)carbonyl]-N-[4,6-bis(diethylamino)-1,3,5-triazin-2-yl]piperazine, (−)-N'-[(pyrrolidin-1-tertbutoxycarbonyl-2-yl)carbonyl]-N-[3,6-bis(diethylamino)pyridin-2-yl]piperazine, $[\alpha]_D=-19.3°$ (c=2.07 in EtOH), (+)-N'-[(pyrrolidin-1-tertbutoxycarbonyl-2-yl)carbonyl]-N-[3,6-bis(diethylamino)pyridin-2-yl]piperazine, $[\alpha]_D=+19.8°$ (c=2.01 in EtOH), N'-[(pyrrolidin-1-tertbutoxycarbonyl-2-yl)carbonyl]-N-[3,6-bis(pyrrolidin-1-yl)pyridin-2-yl]piperazine, N'-[(pyrrolidin-1-tertbutoxycarbonyl-2-yl)carbonyl]-N-[3,6-bis(allylamino)pyridin-2-yl]piperazine, N'-[(pyrrolidin-1-tertbutoxycarbonyl-2-yl)carbonyl]-N-[3,6-bis(N-ethyl-N-allylamino)pyridin-2-yl]piperazine, N'-[(pyrrolidin-1-tertbutoxycarbonyl-2-yl)carbonyl]-N-[3-ethylaminopyridin-2-yl]piperazine.

EXAMPLE 3

2.54 ml of trifluoroacetic acid are added, under stirring and inert gas atmosphere, to a solution of 1.4 g of (−)-N'-[(pyrrolidin-1-tertbutoxycarbonyl-2-yl)carbonyl]-N-[4,6-bis(pyrrolidin-1-yl)-1,3,5-triazin-2-yl]piperazine in 10 ml of methylene chloride.

After 3 hours at room temperature, the reaction mixture is added with 1N NaOH to basic pH, then it is extracted with methylene chloride and repeatedly washed with water. The combined organic extracts are dried over sodium sulfate and the solvent is evaporated off under reduced pressure. The crude product is crystallized from ethyl ether, to give 950 mg of (−)-N'-[(pyrrolidin-2-yl)carbonyl]-N-[4,6-bis(pyrrolidin-1-yl)-1,3,5-triazin-2-yl]piperazine, m.p. 143° C., $[\alpha]_D=-65.75°$ (c=0.23 in EtOH).

EXAMPLE 4

By reacting the N,N'-disubstituted piperazine described in example 2 according to the procedure described in example 3, the following N'-substituted N-[(pyrrolidin-2-yl)carbonyl]piperazines are obtained:

N'-[(pyrrolidin-2-yl)carbonyl]-N-[2,6-bis(diethylamino)pyrimidin-4-yl]piperazine, N'-[(pyrrolidin-2-yl)carbonyl]-N-[2,6-bis(allylamino)-pyrimidin-4-yl]piperazine, (−)-N'-[(pyrrolidin-2-yl)carbonyl]-N-[2,6-bis(pyrrolidin-1-yl)pyrimidin-4-yl]piperazine, m.p. 172°–174° C., $[\alpha]_D=-56.6°$ (c=1.88 in EtOH), (+)-N'-[(pyrrolidin-2-yl)carbonyl]-N-[2,6-bis(pyrrolidin-1-yl)pyrimidin-4-yl]piperazine, m.p. 148°–151° C., $[\alpha]_D=$ +53.5° (c=2.02 in EtOH), N'-[(pyrrolidin-2-yl)carbonyl]-N-[2,6-bis(pyrrolidin-1-yl)pyrimidin-4-yl ]piperazine, m.p. 137° C., N'-[(pyrrolidin-2-yl)carbonyl]-N-[4,6-bis(allylamino)1,3,5-triazin-2-yl]piperazine, N'-[(pyrrolidin-2-yl)carbonyl]-N-[4,6-bis(diethylamino)-1,3,5-triazin-2-yl]piperazine, (–)-N'-[(pyrrolidin-2-yl)carbonyl]-N-[3,6-bis(diethylamino)pyridin-2-yl]piperazine, oil $[\alpha]_D=-43.3°$ (c=2.56 in EtOH), (+)-N'-[(pyrrolidin-2-yl)carbonyl]-N-[3,6-bis(diethylamino)pyridin-2-yl]piperazine, $[\alpha]_D=+48.4°$ (c=2.01 in EtOH), N'-[(pyrrolidin-2-yl)carbonyl]-N-[3,6-bis(pyrrolidin-1yl)pyridin-2-yl]piperazine, N'-[(pyrrolidin-2-yl)carbonyl]-N-[3,6-bis(allylamino)pyridin-2-yl]piperazine, N'-[(pyrrolidin-2 -yl)carbonyl]-N-[3,6-bis(N-ethyl-N-allylamino)pyridin-2-yl]piperazine, N'-[(pyrrolidin-2-yl)carbonyl]-N-[3 -ethylaminopyridin-2 -yl]piperazine.

EXAMPLE 5

0.8 g of (–)-N'-[(pyrrolidin-2-yl)carbonyl]-N-[4,6-bis(pyrrolidin-1-yl)-1,3,5-triazin-2-yl]piperazine dissolved in 20 ml of acetonitrile are added, at 0° C. and under stirring, with 0.22 g of potassium bicarbonate and with a solution of 0.28 ml of ethyl malonyl chloride in 5 ml of acetonitrile. After 4 hours at room temperature and under stirring, the reaction mixture is added with water (50 ml) and extracted repeatedly with ethyl acetate (3×20 ml). The combined organic extracts are dried over sodium sulfate and solvent is evaporated off under reduced pressure. The residue (0.86 g) is purified by silica gel chromatography (eluent hexane/AcOEt 1:1) to give 0.6 g of (–)-N'-[(1-ethoxymalonylpyrrolidin-2-yl)carbonyl]-N-[4,6-bis(pyrrolidin-1-yl)-1,3,5-triazin-2-yl]piperazine, m.p. 115° C., $[\alpha]_D=-23.95°$ (c=0.2 in EtOH).

EXAMPLE 6

According to the procedure described in example 5, starting from the N,N'-disubstituted piperazines described in example 4 and from the malonic acids monoester acid chlorides, optionally 2,2 disubstituted, the following piperazines are prepared:

N'-[(1-ethoxymalonylpyrrolidin-2-yl)carbonyl]-N-[2,6-bis(diethylamino)pyrimidin-4-yl]piperazine, N'-[(1-ethoxymalonylpyrrolidin-2-yl)carbonyl]-N-[2,6-bis(allylamino)pyrimidin-4 -yl]piperazine, (–)-N'-[(1-ethoxymalonylpyrrolidin-2-yl)carbonyl]-N-[2,6-bis(pyrrolidin-1-yl)pyrimidin-4-yl]piperazine, m.p. 170°–172° C., $[\alpha]_D=-26.5°$ (c=2.19 in EtOH), (+)-N'-[(1-ethoxymalonylpyrrolidin-2-yl)carbonyl]-N-[2,6-bis(pyrrolidin-1-yl)pyrimidin-4-yl]piperazine, m.p. 133°–135° C., $[\alpha]_D=+26.5°$ (c=2.14 in EtOH), N'-[(1-ethoxymalonylpyrrolidin-2-yl)carbonyl]-N-[2,6-bis(pyrrolidin-1-yl)pyrimidin-4-yl]piperazine, m.p. 127–129° C., N'-[(1-ethoxymalonylpyrrolidin-2-yl)carbonyl]-N-[4,6-bis(allylamino)-1,3,5-triazin-2-yl ]piperazine, N'-[(1-ethoxymalonylpyrrolidin-2-yl)carbonyl]-N-[4,6-bis(diethylamino)-1,3,5-triazin-2-yl]piperazine, (–)-N'-[(1-ethoxymalonylpyrrolidin-2-yl)carbonyl]-N-[3,6-bis(diethylamino)pyridin-2-yl]piperazine, m.p. hydrochloride 80°–85° C., $[\alpha]_D=-20.6°$ (free base, c=2.09 in EtOH), (+)-N'-[(1-ethoxymalonylpyrrolidin-2 -yl)carbonyl]-N-[3,6-bis(diethylamino)pyridin-2-yl]piperazine, $[\alpha]_D=+20.1°$ (c=2.01 in EtOH), N'-[(1-ethoxymalonylpyrrolidin-2-yl)carbonyl]-N-[3,6-bis(pyrrolidin-1-yl)pyridin-2-yl]piperazine, N'-[(1-ethoxymalonylpyrrolidin-2-yl)carbonyl]-N-[3,6-bis-(allylamino)pyridin-2-yl]piperazine, N'-[(1-ethoxymalonylpyrrolidin-2-yl)carbonyl]-N-[3,6-bis(N-ethyl-N-allylamino)pyridin-2-yl]piperazine, N'-[(1-ethoxymalonylpyrrolidin-2-yl)carbonyl]-N-[3ethylaminopyridin-2 -yl]piperazine, N'-[(1-benzyloxymalonylpyrrolidin-2-yl)carbonyl]-N-[2,6-bis(diethylamino)pyrimidin-4-yl]piperazine, N'-[(1-benzyloxymalonylpyrrolidin-2-yl)carbonyl]-N-[2,6-bis(allylamino)pyrimidin-4-yl]piperazine, (–)-N'-[(1-benzyloxymalonylpyrrolidin-2-yl)carbonyl]-N-[2,6-bis(pyrrolidin-1-yl)pyrimidin-4-yl]piperazine, m.p. 144°–145° C., $[\alpha]_D=-26.5°$ (c=0.23 in EtOH), N'-[(1-benzyloxymalonylpyrrolidin-2-yl)carbonyl]-N-[4,6-bis(allylamino)-1,3,5-triazin-2-yl]piperazine, N'-[(1-benzyloxymalonylpyrrolidin-2-yl)carbonyl]-N-[4,6-bis(diethylamino)-1,3,5-triazin-2-yl]piperazine, N'-[(1-benzyloxymalonylpyrrolidin-2-yl)carbonyl]-N-[4,6-bis(pyrrolidin-1-yl)-1,3,5-triazin-2-yl]piperazine, N'-[(1-benzyloxymalonylpyrrolidin-2-yl) carbonyl]-N-[3,6-bis(diethylamino)pyridin-2-yl]piperazine, N'-[(1-benzyloxymalonylpyrrolidin-2-yl)carbonyl]-N-[3,6-bis(pyrrolidin-1-yl)pyridin-2-yl]piperazine, N'-[(1 -benzyloxymalonylpyrrolidin-2-yl)carbonyl]-N-[3,6-bis(allylamino)pyridin-2-yl]piperazine, N'-[(1-benzyloxymalonylpyrrolidin-2-yl)carbonyl]-N-[3,6-bis(N-ethyl-N-allylamino)pyridin-2-yl]piperazine, N'-[(1-benzyloxymalonylpyrrolidin-2-yl)carbonyl]-N-[3-ethylaminopyridin-2-yl]piperazine, N'-[(1-((2', 2'-dimethyl)benzyloxymalonyl)pyrrolidin-2-yl) carbonyl]-N-[2,6 -bis(diethylamino)pyrimidin-4-yl]piperazine, N'-[(1-((2',2'-dimethyl)benzyloxymalonyl)pyrrolidin-2-yl) carbonyl]-N-[2,6-bis(allylamino)pyrimidin-4-yl ]piperazine, (–)-N'-[(1-((2',2'-dimethyl)benzyloxymalonyl)pyrrolidin -2-yl)carbonyl]-N-[2,6-bis(pyrrolidin-1-yl)pyrimidin -4-yl]piperazine, m.p. 104°–106° C., $[\alpha]_D=-43.2°$ (c=0.24 in EtOH), N'-[(1-((2',2'-dimethyl)benzyloxymalonyl)pyrrolidin-2-yl) carbonyl]-N-[4,6-bis(allylamino)-1,3,5-triazin-2-yl]piperazine, N'-[(1-((2',2'-dimethyl)benzyloxymalonyl)pyrrolidin-2-yl) carbonyl]-N-[4,6-bis(diethylamino)-1,3,5-triazin-2-yl] piperazine, N'-[(1-((2',2'-dimethyl)benzyloxymalonyl)pyrrolidin-2-yl) carbonyl]-N-[3,6-bis(diethylamino)pyridin-2-yl]piperazine, N'-[(1((2',2'-dimethyl)benzyloxymalonyl)pyrrolidin-2-yl) carbonyl]-N-[3,6-bis(pyrrolidin-1-yl) pyridin-2-yl)]piperazine, N'-[(1-((2',2'-dimethyl)benzyloxymalonyl)pyrrolidin-2-yl) carbonyl]-N-[3,6-bis(allylamino)pyridin-2-yl]piperazine, N'-[(1-((2',2'-dimethyl)benzyloxymalonyl)pyrrolidin-2-yl) carbonyl]-N-[3,6-bis(N-ethyl-N-allylamino) pyridin-2-yl]piperazine, N'-[(1-((2',2'-dimethyl)benzyloxymalonyl)pyrrolidin-2-yl) carbonyl]-N-[3-ethylaminopyridin-2-yl]piperazine.

EXAMPLE 7

A solution of 0.5 g of (−)-N'-[(1ethoxymalonylpyrrolidin-2-yl)carbonyl]-N-[4,6-bis(pyrrolidin-yl)-1,3,5-triazin-2-yl]piperazine in 5 ml of methanol is added, under stirring and inert gas atmosphere, with 80 µl of sodium hydroxide (35% aqueous solution). Stirring is continued for 20 more hours, then the reaction mixture is brought to neutrality by addition of sodium bicarbonate, filtered over celite and the solvent is evaporated off under reduced pressure. The crude product (0.52 g) is purified by silica gel chromatography (eluent methylene chloride/methanol 9:1) to obtain 0.43 g of (−)-N'-[(1-malonyl) pyrrolidin -2-yl) carbonyl]-N-[4,6-bis(pyrrolidin -1-yl)-1,3,5-triazin-2-yl]piperazine, m.p. 208°–211° C., $[\alpha]_D$=21.7° (c=0.3 in EtOH).

EXAMPLE 8

1.5 g of (−)-N'-[(1-benzyloxymalonylpyrrolidin-2-yl)carbonyl]-N-[2,6-bis(pyrrolidin-1-yl)pyrimidin-4-yl]piperazine are dissolved in a mixture of 20 ml of methanol and 6 ml of toluene, then 1.5 g of 10% palladium on charcoal are carefully added, under nitrogen protection. The resulting reaction mixture is subjected to catalytic hydrogenation under atmospheric pressure, using an apparatus such as the one described in VOGEL's Textbook of Practical Organic Chemistry, fifth Edition, Longman Scientific & Technical (USA John Wiley & Sons, Inc.), 1989, pages 89–92. After 10 minutes the reaction is filtered through a celite plug to remove the catalyst and the solvent is evaporated off under reduced pressure. By crystallization of the crude product from ethyl ether (5 r), 1.1 g of (−)-N'-[(1-(1'-malonyl)pyrrolidin-2-yl) carbonyl]-N-[2,6-bis-(pyrrolidin -1-yl)pyrimidin-4-yl]piperazine are obtained, m.p. 205°–207° C., $[\alpha]_D$= −19.25° (c=0.21 in EtOH).

EXAMPLE 9

Following the procedures described in example 7 or in example 8, starting from the suitable esters described in example 6, the following carboxylic acids are prepared:

N'-[(1-(1'-malonyl)pyrrolidin-2-yl)carbonyl]-N-[2,6-bis(diethylamino)pyrimidin-4-yl]piperazine, m.p. 193°–195° C., N'-[(1-(1'-malonyl)pyrrolidin-2-yl)carbonyl]-N-[2,6-bis(allylamino)pyrimidin-4-yl]piperazine, N'-[(1-(1'-malonyl)pyrrolidin-2-yl)carbonyl]-N-[4,6-bis(allylamino)-1,3,5-triazin-2-yl]piperazine, m.p. 200°–201° C., N'-[(1-(1'-malonyl)pyrrolidin-2-yl) carbonyl]-N-[4,6-bis(diethylamino)-1,3,5-triazin-2-yl]piperazine, N'-[(1-(1'-malonyl)pyrrolidin-2-yl)carbonyl]-N-[3,6-bis(diethylamino)pyridin-2-yl]piperazine, m.p. sodium salt, 188°–191° C., N'-[(1-(1'-malonyl)pyrrolidin-2-yl) carbonyl]-N-[3,6-bis(pyrrolidin-1-yl)pyridin-2-yl]piperazine, N'-[(1-(1'-malonyl)pyrrolidin-2-yl)carbonyl]-N-[3,6-bis(allylamino)pyridin-2-yl]piperazine, m.p. potassium salt, 179°–180° C., N'-[(1-(1'-malonyl)pyrrolidin-2-yl)carbonyl ]-N-[3,6-bis(N-ethyl-N-allylamino)pyridin-2-yl]piperazine, N'-[(1-(1'-malonyl)pyrrolidin-2-yl)carbonyl ]-N-[3ethylaminopyridin-2-yl]piperazine, m.p. sodium salt 171°–174° C., N'-[(1-(2',2'-dimethyl-1'-malonyl) pyrrolidin-2-yl)carbonyl]-N-[2,6-bis(diethylamino)pyrimidin-4yl]piperazine, m.p. 166°–168° C., N'-[(1-(2',2'-dimethyl-1'-malonyl)pyrrolidin-2-yl)carbonyl]-N-[2,6-bis(allylamino)pyrimidin-4-yl]piperazine, (−)-N'-[((1(2',2'-dimethyl-1'-malonyl)pyrrolidin 2-yl)carbonyl]-N-[2,6-bis(pyrrolidin-1-yl) pyrimidin-4-yl]piperazine, m.p. 160°–163° C., $[\alpha]_D$=−28.4° (c=0.2 in EtOH), N'-[(1-(2',2'-dimethyl-1'-malonyl)pyrrolidin-2-yl)carbonyl]-N-[4,6-bis(allylamino)-1,3,5-triazin-2-yl]piperazine, m.p. 170°–172° C., N'-[(1(2',2'-dimethyl-1'-malonyl)pyrrolidin-2-yl)carbonyl]-N-[4,6-bis(diethylamino)-1,3,5-triazin-2-yl]piperazine, N'-[(1(2',2'-dimethyl-1'-malonyl)pyrrolidin-2-yl)carbonyl]-N-[4,6-bis(pyrrolidin-1yl)-1,3,5-triazin-2yl]piperazine, m.p. 180°–181° C., N'-[(1(2',2'-dimethyl-1'-malonyl)pyrrolidin-2-yl)carbonyl]-N-[3,6-bis(diethylamino)pyridin-2-yl]piperazine, m.p. sodium salt 189°–192° C., N'-[(1-(2',2'-dimethyl-1'-malonyl)pyrrolidin-2-yl)carbonyl]-N-[3,6-bis(pyrrolidin-1-yl)pyridin-2-yl]piperazine, N'-[(1-(2',2'-dimethyl-1'-malonyl)pyrrolidin-2-yl)carbonyl]-N-[3,6-bis(allylamino)pyridin-2-yl]piperazine, N'-[(1-(2',2'-dimethyl-1'-malonyl)pyrrolidin-2-yl)carbonyl]-N-[3,6-bis(N-ethyl-N-allylamino)pyridin-2-yl]piperazine, m.p. potassium salt 195°–200° C., N'-[(1-(2',2'-dimethyl-1'-malonyl)pyrrolidin-2-yl)carbonyl]-N-[3-ethylaminopyridin-2-yl]piperazine, m.p. potassium salt 206°–208° C.

EXAMPLE 10

A solution of BOC-(L)-proline in 60 ml of anhydrous THF, cooled at −10° C. with brine, is added with 6.1 ml of triethylamine and 1 g of 4 A molecular sieves, then, keeping the temperature below −5° C., a solution of 4.16 ml of ethyl chloroformate in 5 ml of anhydrous THF is dropped therein. After 30 minutes under stirring, the reaction mixture is filtered to remove the triethylammonium chloride precipitate and the filtrate is concentrated under reduced pressure to a volume of 30 ml. The resulting solution is dropped into a suspension of 7.5 g of sodium borohydride in 50 ml of anhydrous THF, cooled at −10° C. with brine. After 2 hours the reaction mixture is added with 200 ml of an aqueous saturated solution of sodium dihydrogen phosphate, keeping the temperature at 0° C. with water/ice, then it is extracted with ethyl acetate (3×50 ml). The combined organic extracts are washed repeatedly with an aqueous saturated solution of sodium bicarbonate (3×30 ml), dried over sodium sulfate and the solvent is evaporated off under reduced pressure. The residue, by crystallization from hexane, yields 6.1 g of BOC-(L)-prolinol, m.p. 59°–60° C., $[\alpha]_D$=−54.9° (c=0.2 in EtOH).

EXAMPLE 11

A solution of 3 g of BOC-(L)-prolinol in 100 ml of anhydrous THF, cooled at 0° C. with water/ice, under stirring and inert gas atmosphere, is added with 2.9 g of carbonyldiimidazole in portions, then the reaction mixture is warmed to room temperature and stirring is continued for 3 hours. Said solution is added with 4.5 g of N-[2,6-bis(pyrrolidin-1-yl)pyrimidin-4-yl]piperazine in portions and stirring is continued for 18 hours. The reaction mixture is added with 400 ml of an aqueous saturated solution of sodium dihydrogen phosphate and extracted with ethyl acetate (3×100 ml). The combined organic extracts are dried over sodium sulfate and the solvent is evaporated off under reduced pressure. The residue (7.5 g) is purified by silica gel chromatography (eluent hexane/ethyl acetate 7:3), to obtain 5.5 g of (−)-N'-[(1-(tertbutoxycarbonyl) pyrrolidin-2-yl)

methyloxycarbonyl]-N-[2,6-bis(pyrrolidin -1-yl)pyrimidin -4 -yl]piperazine, m.p. 147° C., [(α]D-32'(c=0.25 in EtOH).

EXAMPLE 12

17.4 ml of trifluoroacetic acid are dropped into a solution of 10 g of (−)-N'-[(1-(tertbutoxycarbonyl) pyrrolidin-2-yl-)methyloxycarbonyl ]-N-[2,6bis(pyrrolidin-1-yl)pyrimidin-4-yl]piperazine in 300 ml of methylene chloride. After about 18 hours, the reaction mixture is added with 400 ml of a 1N sodium hydroxide aqueous solution and extracted with methylene chloride (3×150 ml). The combined organic extracts are washed with water (2×100 ml), dried over sodium sulfate and the solvent is evaporated off under reduced pressure. By crystallization of the residue from diisopropyl ether/ethyl acetate 9:1, 6.5 g of (−)-N'-[(pyrrolidin-2-yl)methyloxycarbonyl]-N-[2,6-bis(pyrrolidin) -1-yl)pyrimidin-4-yl]piperazine are obtained, m.p. 137°–138° C., [α]$_D$=−8.7° (c=0.23 in EtOH).

EXAMPLE 13

A solution of 3.4 g of 2,2-dimethylmalonic acid monobenzyl ester in 75 ml of anhydrous dimethyl formamide, cooled at 0° C. with brine, under stirring and inert gas atmosphere, is added with 3.77 g of 1-hydroxybenzotriazole, 1.55 ml of N-methylmorpholine, 6 g of (−)-N'-[(pyrrolidin-2-yl)methyloxycarbonyl]-N-[2,6 -bis(pyrrolidin -1-yl)pyrimidin-4-yl]piperazine and finally 5.35 g of N'-(3-dimethylaminopropyl-N-ethylcarbodiimide hydrochloride dissolved in 25 ml of dimethylformamide, in this succession. The mixture is left to warm to room temperature, then stirring is continued for 18 more hours. The solvent is evaporated off under reduced pressure, then the reaction mixture is added with 200 ml of a sodium bicarbonate saturated aqueous solution and extracted with ethyl acetate (3×100 ml). The combined organic extracts are dried over sodium sulfate and the solvent is evaporated off under reduced pressure. 10.2 g of a crude product are obtained, which is purified by silica gel chromatography (300 g of silica eluent petroleum ether/ethyl acetate 1:1), to obtain 6.5 g of (−)-N'-[(1-(3'-benzyloxy-2',2'-dimethylmalon-1'-yl)pyrrolidin-2-yl)methyloxycarbonyl]-N-[2,6-bis(pyrrolidin-1-yl)pyrimidin-4-yl] piperazine, as a light brown foam. 6.45 g of (−)-N'-[(1-(3'-benzyloxy-2',2'-dimethylmalon-1'-yl)pyrrolidin-2-yl)methyloxycarbonyl]-N-[2,6-bis(pyrrolidin-1-yl)pyrimidin-4-yl]piperazine are dissolved in a mixture of 100 ml of methanol and 40 ml of toluene. Said solution is carefully added with 0.65 g of 10% palladium on charcoal and the resulting reaction mixture is subjected to catalytic hydrogenation under atmospheric pressure using an apparatus such as the one described in VOGEL's Textbook of Practical Organic Chemistry, fifth Edition, Longman Scientific & Technical (USA John Wiley & Sons, Inc.), 1989, pages 89–92. After 10 minutes the reaction is filtered through a celite plug to remove the catalyst and the solvent is evaporated off under reduced pressure. By crystallization of the crude product from diisopropyl ether, 5.5 g of (−)-N'-[(1-(2',2'-dimethylmalon-1'-yl)pyrrolidin-2-yl)methyloxycarbonyl]-N-[2,6-bis(pyrrolidin-1-yl)pyrimidin-4-yl]piperazine are obtained, m.p. 159°–160° C., [α]$_D$=−49.8° (c=0.21 in EtOH).

EXAMPLE 14

Following the procedures described in the examples 11, 12 and 13, starting from the suitable N-substituted piperazines and from the suitable malonic acids monoalkyl or mono-benzyl esters, optionally 2,2-disubstituted, the following N,N'-disubstituted piperazines are obtained:

N'-[(1 -(1'-malonyl)pyrrolidin-2-yl)methyloxycarbonyl]-N-[2,6-bis(diethylamino)pyrimidin-4-yl]piperazine, m.p. 168°–170° C., N'-[(1-(1'-malonyl)pyrrolidin-2-yl)methyloxycarbonyl ]-N-[2,6 -bis(allylamino)pyrimidin -4 -yl]piperazine, (−)-N'-[(1-(1'-malonyl)pyrrolidin-2-yl)methyloxycarbonyl]-N-[2,6-bis(pyrrolidin-1-yl)pyrimidin-4-yl]piperazine, m.p. 169°–170° C., [α]$_D$=−38.1'(c=0.2 in EtOH), N'-[(1-(1'-malonyl)pyrrolidin-2-yl)methyloxycarbonyl]-N-[4,6-bis(allylamino)-1,3,5-triazin-2-yl]piperazine, m.p. 177°–181° C., N'-[(1-(1'-malonyl)pyrrolidin-2-yl)methyloxycarbonyl]-N-[4,6-bis(diethylamino)-1,3,5-triazin-2-yl]piperazine, N'-[(1-(1'-malonyl)pyrrolidin-2-yl)methyloxycarbonyl]-N-[3,6-bis(diethylamino)pyridin-2-yl]piperazine, m.p. sodium salt 198°–199° C., N'-[(1-(1'-malonyl)pyrrolidin-2-yl)methyloxycarbonyl]-N-[3,6-bis(pyrrolidin-1-yl)pyridin-2-yl]piperazine, m.p. sodium salt 203°–205° C., N'-[(1-(1'-malonyl)pyrrolidin-2-yl)methyloxycarbonyl]-N-[3,6-bis(allylamino)pyridin-2-yl]piperazine, N'-[(1-(1'-malonyl)pyrrolidin-2-yl)methyloxycarbonyl]-N-[3,6-bis(N-ethyl-N-allylamino)pyridin-2-yl]piperazine, N'-[(1-(1'-malonyl)pyrrolidin-2-yl)methyloxycarbonyl]-N-[3-ethylaminopyridin-2-yl]piperazine, m.p. sodium salt 200°–201° C., N'-[(1-(2',2'-dimethyl-1'-malonyl)pyrrolidin-2-yl)methyloxycarbonyl]-N-[2,6-bis(diethylamino) pyrimidin-4yl] piperazine, N'-[(1-(2',2'-dimethyl-1'-malonyl)pyrrolidin-2-yl)methyloxycarbonyl]-N-[2,6 -bis(allylamino)pyrimidin-4yl]piperazine, m.p. 161°–162° C., N'-[(1-(2',2'-dimethyl-1'-malonyl) pyrrolidin-2-yl)-methyloxycarbonyl]-N-[4,6-bis(allylamino)-1,3,5-triazin-2-yl] piperazine, m.p. 167°–170° C., N'-[(1-(2',2'-dimethyl-1'-malonyl)pyrrolidin-2-yl)-methyloxycarbonyl]-N-[4,6-bis(diethylamino)-1,3,5-triazin-2-yl]piperazine, N'-[(1-(2',2'-dimethyl-1'-malonyl)pyrrolidin- 2-yl)-methyloxycarbonyl]-N-[4,6-bis(pyrrolidin-1-yl)-1,3,5-triazin-2-yl]piperazine, m.p. 172°–173° C., N'-[(1-(2',2'-dimethyl-1'-malonyl)pyrrolidin-2-yl)methyloxycarbonyl]-N-[3,6-bis(diethylamino)pyridin-2-yl]piperazine, N'-[(1-(2',2'-dimethyl-1'-malonyl)pyrrolidin-2-yl)methyloxycarbonyl]-N-[3,6-bis(pyrrolidin-1-yl)pyridin-2-yl] piperazine, m.p. potassium salt 206°–209° C., N'-[(1-(2',2'-dimethyl-1'-malonyl)pyrrolidin-2-yl)methyloxycarbonyl]-N-[3,6-bis(allylamino)pyridin-2yl]piperazine, N'-[(1(2',2'-dimethyl-1'-malonyl)pyrrolidin- 2-yl)methyloxycarbonyl]-N-[3,6-bis (N-ethyl-N-allylamino)-pyridin-2-yl]piperazine, m.p. sodium salt 210°–213° C., N'-[(1(2',2'-dimethyl-1'-malonyl)pyrrolidin-2 -yl)methyloxycarbonyl]-N-[3-ethylaminopyridin-2-yl]piperazine, m.p. potassium salt 220°–225° C.

We claim:

1. Compounds of general formula (I)

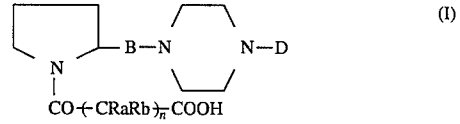

the single enantiomeric and diastereomeric forms thereof, the mixtures thereof and the pharmaceutically acceptable salts thereof with pharmaceutically acceptable acids and bases, wherein:

B is a —CO—, —CH$_2$OCO—, —CH$_2$OCS—, —CH$_2$NHCO—, —CH$_2$NHCS— group;

D is a 5–6 membered heterocycle having 3–5 carbon atoms and 1–3 nitrogen atoms in the ring, the heterocycle being unsubstituted or substituted with 1 or 2 amino, mono-C$_1$–C$_6$alkylamino, mono-C$_3$–C$_7$-alkenyl- or mono-C$_3$–C$_7$alkynylamino, di-C$_1$–C$_6$-alkylamino, (C$_1$–C$_6$)alkyl (C$_3$C$_7$)alkenylamino, piperidin-1-yl, morpholin-4-yl or pyrrolidin-1-yl groups;

Ra and Rb are independently hydrogen or C$_1$–C$_3$ alkyl or, taken together with the carbon atom to which they are linked, form a C$_3$–C$_6$-cycloalkyl group; and n is an integer from 1 to 4.

2. Compounds according to claim 1, wherein as D is selected from [2,6-bis(diethylamino)-4-pyrimidinyl], [2,6-bis(allylamino)-4-pyrimidinyl], [2,6-bis(amino)-4-pyrimidinyl], [2,6-bis(pyrrolidin-1-yl)-4-pyrimidinyl], [4,6-bis(allylamino)-1,3,5-triazin-2-yl], [4,6-bis-(diethylamino)-1,3,5-triazin-2-yl], [4,6-bis(pyrrolidin-1-yl)-1,3,5-triazin-2-yl], [3,6-bis(diethylamino)-pyridin-2-yl], [3,6-bis(pyrrolidin-1-yl)pyridin-2-yl], [3,6-bis(allylamino)pyridin-2-yl], [3,6-bis(propargylamino)pyridin-2-yl], [3,6-bis(N-ethyl-N-allylamino)pyridin-2-yl], [3-ethylaminopyridin-2-yl].

3. Compounds according to claim 1, wherein B is a —CO— or —CH$_2$OCO— group; D is heterocycle selected from [2,6-bis(pyrrolidin-1-yl)-4-pyrimidinyl], [4,6-bis(pyrrolidin-1-yl)-1,3,5-triazin-2-yl], [3,6-bis(diethylamino)pyridin-2-yl] and [3-ethylaminopyridin-2-yl]; Ra, which is the same as Rb, is hydrogen or methyl and n=1.

4. A process for the preparation of the compounds of the compounds claim 1, characterized in that a compound of formula (II)

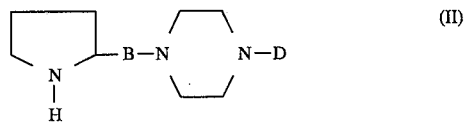

wherein B and D are as defined above, is reacted with a compound of formula (III)

wherein Ra, Rb and n have the above described meanings;

R is a leaving group which can easily be removed; E is chlorine, bromine, N-imidazolyl, OH, O-hydroxysuccinimidyl or, taken together with the carbonyl group, it forms a mixed anhydride with a carboxylic or sulfonic acid, to give compounds of formula (Ia)

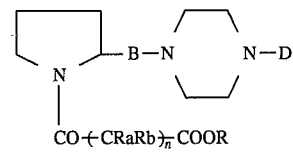

and the R group is removed from the compound of formula (Ia) to produce the compounds of formula (I).

5. A process according to claim 4, characterized in that the compounds of formula (Ia)

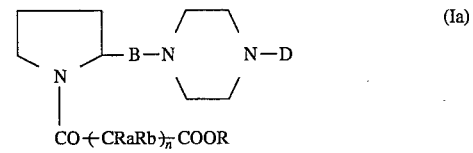

wherein B, D, Ra, Rb and n are as defined above and R is C$_1$–C$_6$ alkyl are hydrolyzed with mineral bases in suitable concentrations and in a suitable solvent to produce the compounds of formula (I).

6. A process according to claim 4, characterized in that the compounds of formula (Ia)

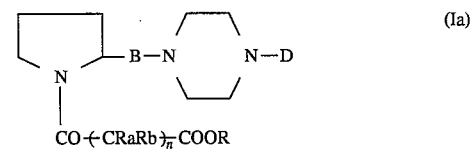

wherein B, D, Ra, Rb and n are as defined above and R is allyl or benzyl, are catalytically hydrogenated to produce the compounds of formula (I).

7. A process according to claim 6, characterized in that hydrogenation is carried out with a catalyst selected from palladium on charcoal in various concentrations, nikel-Raney, palladium tetrakis(triphenylphosphine) in a suitable solvent or by means of hydrogen transfer procedures.

8. Pharmaceutical compositions containing a compound of claim 1 as the active ingredient.

9. A method of treating asthmatic or inflammatory conditions of the respiratory tract in a patient in need of such treatment, comprising administering to the patient an asthmatic-condition-treating or inflammatory-condition-treating effective amount of a compound of claim 1.

10. A method according to claim 9, wherein the compound is administered in a dosage of 2–50 µg/kg.

11. A method according to claim 9, wherein the compound is administered at a daily dose of 1–50 mg.

12. A method according to claim 11, wherein the daily dose is divided into a plurality of individual doses.

* * * * *